United States Patent
Heinemann et al.

(10) Patent No.: US 6,262,051 B1
(45) Date of Patent: *Jul. 17, 2001

(54) FUNGICIDAL METHOXIMINOMETHYLDIOXAZINES

(75) Inventors: Ulrich Heinemann, Leichlingen; Herbert Gayer, Monheim; Peter Gerdes, Aachen; Bernd-Wieland Krüger, Bergisch Gladbach; Robert Markert, Köln; Thomas Seitz, Langenfeld; Bernd Gallenkamp, Wuppertal; Uwe Stelzer, Burscheid; Ralf Tiemann, Leverkusen; Astrid Mauler-Machnik, Leichlingen; Stefan Dutzmann, Langenfeld; Klaus Stenzel, Düsseldorf; Gerd Hänssler, Leverkusen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,068
(22) PCT Filed: Mar. 23, 1998
(86) PCT No.: PCT/EP98/01667
   § 371 Date: Sep. 28, 1999
   § 102(e) Date: Sep. 28, 1999
(87) PCT Pub. No.: WO98/45289
   PCT Pub. Date: Oct. 15, 1998

(30) Foreign Application Priority Data

Apr. 3, 1997 (DE) .............................................. 197 13 762

(51) Int. Cl.$^7$ ...................... A61K 31/539; C07D 273/01
(52) U.S. Cl. ...................... 514/229.2; 544/65; 544/314; 544/315; 544/317
(58) Field of Search ................................. 514/229.2, 274; 544/312, 315, 317, 65, 657

(56) References Cited

FOREIGN PATENT DOCUMENTS

| 0468684 | * | 7/1991 | (EP) . |
| 95 04728 | * | 2/1995 | (WO) . |
| 95 24396 | * | 9/1995 | (WO) . |
| 97 27187 | * | 7/1997 | (WO) . |

* cited by examiner

Primary Examiner—Richard L. Raymond
Assistant Examiner—Venkataraman Balasubramanian
(74) Attorney, Agent, or Firm—Joseph C. Gil

(57) ABSTRACT

The invention relates to novel methoximinomethyldioxazines,

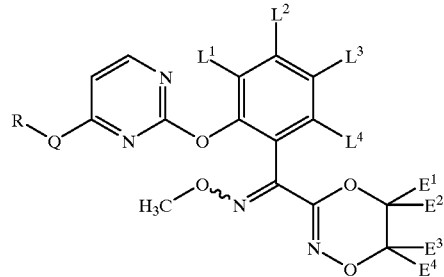

(I)

to a plurality of processes for their preparation and to their use as fungicides, and also to novel intermediates and to a process for their preparation.

7 Claims, No Drawings

FUNGICIDAL METHOXIMINOMETHYLDIOXAZINES

The invention relates to novel methoximinomethyldioxazines, to a plurality of processes for their preparation and to their use as fungicides, and also to novel intermediates and to a process for their preparation.

It is already known that certain methoximinomethyldioxazines, of a similar constitution to those described below, have fungicidal properties (compare, for example, WO-A 9504728). However, the fungicidal activity of these compounds is unsatisfactory, in particular at low application rates.

This invention, accordingly, provides the novel compounds of the general formula (I)

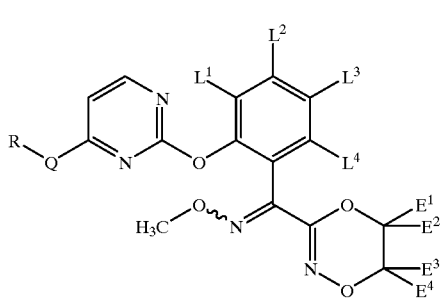

(I)

in which

R represents in each case optionally substituted alkyl, arylalkyl, arylalkenyl, alkenyl, alkinyl or cycloalkyl,

Q represents oxygen, sulphur, —NH— or ,
where $R^1$ represents alkyl, $E^1$, $E^2$, $E^3$ and $E^4$ are identical or different and independently of one another each represents hydrogen, alkyl, halogenoalkyl or hydroxyalkyl, or $E^1$ and $E^2$ or $E^1$ and $E^3$ or $E^3$ and $E^4$ together with the respective carbon atoms to which they are attached form a cycloaliphatic ring and $L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

In the definition, the saturated or unsaturated hydrocarbon chains, such as alkyl, alkanediyl, alkenyl or alkinyl, are in each case straight-chain or branched, including in combination with heteroatoms, such as in alkoxy, alkylthio or alkylamino.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If appropriate, the cyclic compounds form a polycyclic ring system together with other carbocyclic or heterocyclic, fused-on or bridged rings. Preference is given to mono- or bicyclic ring systems, in particular to mono- or bicyclic aromatic ring systems.

Cycloalkyl represents saturated, carbocyclic, cyclic compounds which, if appropriate, form a polycyclic ring system with other carbocyclic, fused-on or bridged rings.

Furthermore, it has been found that the novel methoximinomethyldioxazines of the general formula (I) are obtained when (process a) 4-halogeno-2-phenoxypyrimidines of the general formula (II)

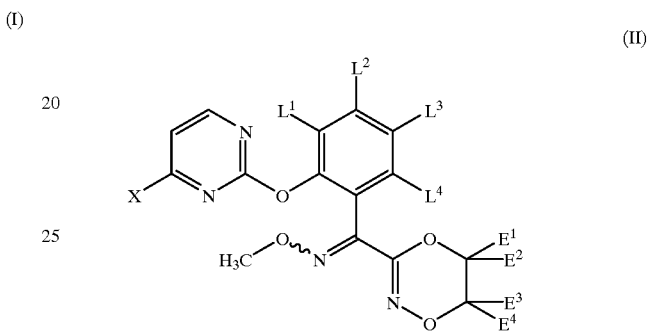

(II)

in which $E^1$, $E^2$, $E^3$, $E^4$, $L^1$, $L^2$, $L^3$ and $L^4$ are as defined above and X represents halogen, in particular chlorine, are reacted with a nucleophilic compound of the general formula

R—Q—H (III), in which

R and Q are as defined above, if appropriate in the presence of a diluent and if appropriate in the presence of an acid acceptor, or when (process b) alkylsulphonylpyrimidines of the general formula (IV)

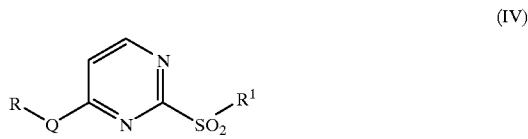

(IV)

in which

R and Q are as defined above and $R^1$ represents alkyl or arylalkyl, are reacted with a 3-(1-hydroxyphenyl-1-methoximinomethyl)dioxazine of the general formula

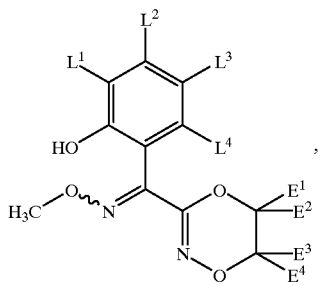
(V)

in which
E¹, E², E³, E⁴, L¹, L², L³ and L⁴ are as defined above,
if appropriate in the presence of a diluent and if appropriate in the presence of an acid acceptor.

Finally, it has been found that the novel methoximinomethyldioxazines of the general formula (I) have very strong fungicidal action.

If appropriate, the compounds according to the invention can be present as mixtures of different possible isomeric forms, in particular of stereoisomers, such as, for example, E and Z, or optical isomers. What is claimed are both the E and the Z isomers, the individual enantiomers, the racemates, and any mixtures of these isomers.

The present application preferably provides compounds of the formula (I) in which R
  represents methyl which is optionally mono- to trisubstituted by halogen and/or monosubstituted by cycloalkyl having 3 to 6 carbon atoms, where the cycloalkyl groups for their part are optionally substituted by 1 to 4 halogen atoms and/or 1 to 3 alkyl groups having 1 to 3 carbon atoms, or
  represents alkyl, alkenyl or alkinyl having 2 to 12 carbon atoms, which is optionally monosubstituted to n-times substituted (where n represents the number of the hydrogen atoms of the unsubstituted hydrocarbon radical in question) by halogen and/or 1 to 2 alkoxy groups having 1 to 8 carbon atoms and/or 1 to 2 cycloalkyl groups having 3 to 6 carbon atoms (where the cycloalkyl groups for their part are optionally substituted by 1 to 4 halogen atoms and/or 1 to 3 alkyl groups having 1 to 3 carbon atoms), or
  represents cycloalkyl having 3 to 8 carbon atoms which is optionally mono- to pentasubstituted by alkyl having 1 to 4 carbon atoms, halogen and/or alkoxy having 1 to 4 carbon atoms or
  represents arylalkyl or arylalkenyl having 1 to 5 carbon atoms in the alkyl moiety and 2 to 5 carbon atoms in the alkenyl moiety, respectively, and 6 to 10 carbon atoms in the aryl moiety, which is optionally mono- to pentasubstituted in the aryl moiety, where the substituents of the aryl moiety are preferably selected from the list below:
  halogen, cyano, nitro, amino, hydroxyl, formyl, carboxyl, carbamoyl, thiocarbamoyl;
  alkyl, alkoxy, alkylthio, alkylsulphinyl or alkylsulphonyl having in each case 1 to 6 carbon atoms;
  alkenyl or alkenyloxy having in each case 2 to 6 carbon atoms;
  halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
  halogenoalkenyl or halogenoalkenyloxy having in each case 2 to 6 carbon atoms and 1 to 11 identical or different halogen atoms;
  alkylamino, dialkylamino, alkylcarbonyl, alkylcarbonyloxy, alkoxy-carbonyl or alkylsulphonyloxy, having in each case 1 to 6 carbon atoms in the individual alkyl moieties;
  in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;
  cycloalkyl having 3 to 8 carbon atoms;
  heterocyclyl or heterocyclyl-methyl having in each case 3 to 7 ring members, 1 to 3 of which are in each case identical or different heteroatoms—in particular nitrogen, oxygen and/or sulphur—or a grouping

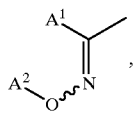

in which
A¹ represents alkyl having 1 to 4 carbon atoms or cycloalkyl having 1 to 6 carbon atoms and
A² represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms,
Q represents oxygen, sulphur, —NH—or

where R¹ represents alkyl having 1 to 4 carbon atoms,
E¹, E², E³ and E⁴ are identical or different and independently of one another represent hydrogen, alkyl or hydroxyalkyl having in each case 1 to 4 carbon atoms or halogenoalkyl having 1 to 4 carbon atoms and 1 to 5 identical or different halogen atoms, or
E¹ and E² or E¹ and E³ or E³ and E⁴ together with the respective carbon atoms to which they are attached form a cycloaliphatic ring having 5, 6 or 7 carbon atoms and
L¹, L², L³ and L⁴ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms.

The present application relates in particular to compounds of the formula (I) in which R
  represents methyl which is optionally mono-, di- or trisubstituted by fluorine, chlorine or bromine and/or monosubstituted by cyclopropyl, cyclobutyl, cyclopentyl or cyclohexyl, where the cycloalkyl groups for their part are optionally substituted by 1 to 4 fluorine, chlorine or bromine atoms and/or 1 to 3 methyl or ethyl groups, or represents ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl, n-heptyl-, n-octyl-, n-nonyl-, n-decyl, n-undecyl, n-dodecyl, allyl, but-2-en-1-yl, but-1-en-3-yl, hex-2-en- 1-yl, hexa-2,4-dien- 1-yl, propargyl, but-2-in- 1-yl, which is optionally monosubstituted to n-times substituted (where n represents the number of the hydrogen atoms of the unsubstituted hydrocarbon radical in question), in particular mono- to trisubstituted, by fluorine, chlorine or bromine and/or mono- to disubstituted by methoxy, ethoxy, cyclopropyl, cyclobutyl, cyclopentyl or cyclohexyl (where the cycloalkyl groups for their part are optionally substituted by 1 to 4 fluorine, chlorine or bromine atoms and/or 1 to 3 methyl or ethyl groups), or represents cyclobutyl, cyclopentyl, cyclohexyl, cycloheptyl or cyclopropyl which is optionally mono- to pentasubstituted by methyl, ethyl, n- or i-propyl, n-, i-, s- or t-butyl, fluorine, chlorine, bromine, methoxy or ethoxy or represents 1-phenylethyl, 2-phenylethyl, 1-phenylpropyl, 2-phenylpropyl, 3-phenylpropyl, 1-phenylprop-2-yl, 2-phenylprop-2-yl, 3-phenylbutyl, 4-phenylbutyl, 5-phenylpentyl, 3-phenylallyl, naphth-1-ylmethyl or naphth-2-ylmethyl or benzyl which is optionally mono- to pentasubstituted in the phenyl or naphthyl moiety, where the substituents of the aryl moiety are preferably selected from the list below:

fluorine, chlorine, bromine, cyano, methyl, ethyl, n- or i-propyl, n-, i-, s- or t-butyl methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents from the group consisting of fluorine, chlorine, methyl, trifluoromethyl and ethyl or a grouping

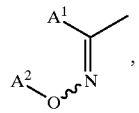

where

A$^1$ represents methyl, ethyl, n- or i-propyl, n-, i-, s- or t-butyl, cyclopropyl or cyclobutyl and A$^2$ represents methyl, ethyl, n- or i-propyl, n-, i-, s- or t-butyl, allyl, propargyl, but-2-en- 1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, Q represents oxygen, sulphur, —NH—,

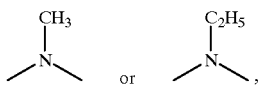

E$^1$, E$^2$, E$^3$ and E$^4$ are identical or different and independently of one another represent hydrogen, methyl, ethyl, n- or i-propyl, n-, i-, s- or t-butyl, hydroxymethyl, trifluoromethyl or trifluoroethyl, or E$^1$ and E$^2$ or E$^1$ and E$^3$ or E$^3$ and E$^4$ together with the respective carbon atoms to which they are attached form a cycloaliphatic ring having 5, 6 or 7 carbon atoms and L$^1$, L$^2$, L$^3$ and L$^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

A particularly preferred group of compounds according to the invention are those compounds of the formula (I) in which

R represents methyl which is optionally mono-, di- or trisubstituted by fluorine, chlorine or bromine and/or monosubstituted by cyclopropyl, cyclobutyl, cyclopentyl or cyclohexyl, where the cycloalkyl groups for their part are optionally substituted by 1 to 4 fluorine, chlorine or bromine atoms and/or 1 to 3 methyl or ethyl groups, or represents ethyl, n- or i-propyl, n-, i-, s- or t-butyl, 1-, 2-, 3-, neopentyl, 1-, 2-, 3-, 4-(2-methylbutyl), 1-, 2-, 3-hexyl, 1-, 2-, 3-, 4-, 5(2-methylpentyl), 1-, 2-, 3-(3-methylpentyl), 2-ethylbutyl, 1-, 3-, 4-(2,2-dimethylbutyl), 1-, 2-(2,3-dimethylbutyl, n-heptyl-, n-octyl-, n-nonyl-, n-decyl, n-undecyl, n-dodecyl, allyl, but-2-en-1-yl, but-1-en-3-yl, hex-2-en-1-yl, hexa-2,4-dien-1-yl, propargyl, but-2-in-1-yl, which is optionally monosubstituted to n-times substituted (where n represents the number of the hydrogen atoms of the unsubstituted hydrocarbon radical in question), in particular mono- to trisubstituted, by fluorine, chlorine or bromine and/or mono- to disubstituted by methoxy, ethoxy, cyclopropyl, cyclobutyl, cyclopentyl or cyclohexyl (where the cycloalkyl groups for their part are optionally substituted by 1 to 4 fluorine, chlorine or bromine atoms and/or 1 to 3 methyl or ethyl groups), or represents cyclobutyl, cyclopentyl, cyclohexyl, cycloheptyl or cyclopropyl which is optionally mono- to pentasubstituted by methyl, ethyl n- or i-propyl, n-, i-, s- or t-butyl, fluorine, chlorine, bromine, methoxy or ethoxy or represents 1-phenylethyl, 2-phenylethyl, 1-phenylpropyl, 2-phenylpropyl, 3-phenylpropyl, 1-phenylprop-2-yl, 2-phenylprop-2-yl, 3-phenylbutyl, 4-phenylbutyl, 5-phenylpentyl, 3-phenylallyl, naphth-1-ylmethyl or naphth-2-ylmethyl or benzyl which is optionally mono- to pentasubstituted in the phenyl or naphthyl moiety, where the substituents of the aryl moiety are preferably selected from the listed below:

fluorine, chlorine, bromine, cyano, methyl, ethyl, n- or i-propyl, n-, i-, s- or t-butyl methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents from the group consisting of fluorine, chlorine, methyl, trifluoromethyl and ethyl or a grouping

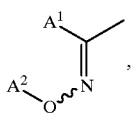

where $A^1$ represents methyl, ethyl, n- or i-propyl, n-, i-, s- or t-butyl, cyclopropyl or cyclobutyl and $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, Q represents oxygen, sulphur, —NH—,

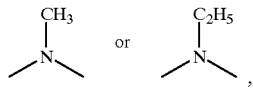

$E^1$ and $E^2$ are identical or different and independently of one another each represents hydrogen or methyl, $E^3$ and $E^4$ represent hydrogen $L^1$ and $L^3$ are identical or different and independently of one another each represents hydrogen or methyl, and $L^2$ and $L^4$ represent hydrogen The abovementioned general or preferred radical definitions apply both to the end products of the formula (I) and, correspondingly, to the starting materials or intermediates required in each case for the preparation.

The radical definitions given in the respective combinations or preferred combinations of radicals specifically for these radicals are, independently of the combination which is given in each case, also replaced as desired by corresponding radical definitions of other preferred ranges.

Preference is given, in particular, to compounds of the formula (I) in which

Q represents oxygen or sulphur and in particular oxygen.

Preference is given, in particular, to compounds of the formula (I) in which

R represents unsubstituted or substituted methyl, ethyl, propyl, pentyl, hexyl, heptyl, octyl, where these radicals are optionally present in straight-chain, branched or cyclic form.

Suitable substituents for these radicals are preferably the substituents given in the application and, in particular, fluorine, chlorine and/or unsubstituted or preferably fluorine-, chlorine-, bromine-, methyl- and/or ethyl-substituted phenyl.

A very particularly preferred group of compounds according to the invention are those compounds of the formula (I) in which $E^1$, $E^2$, $E^3$, $E^4$, $L^1$, $L^2$, $L^3$ and $L^4$ represent hydrogen.

The formula (II) provides a general definition of the 4-halogeno-2-phenoxypyrimidines required as starting materials for carrying out the process a) according to the invention. In this formula (II), $E^1$, $E^2$, $E^3$, $E^4$, $L^1$, $L^2$, $L^3$ and $L^4$ preferably or in particular have those meanings which have already been mentioned in connection with the description of the compounds of the formula (I) according to the invention as being preferred or as being particularly preferred for $E^1$, $E^2$, $E^3$, $E^4$, $L^1$, $L^2$, $L^3$ and $L^4$. X represents halogen, preferably chlorine.

The 4-halogeno-2-phenoxypyrimidines of the formula (II) have as yet not been disclosed; as novel substances, they also form part of the subject matter of the present application.

They are obtained (process c) when 4-halogeno-2-alkylsulphonylpyrimidines of the general formula (VI)

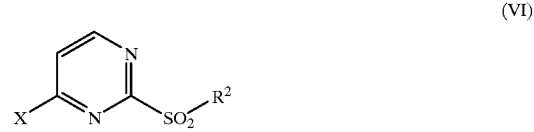

(VI)

in which

X is as defined above and $R^2$ represents alkyl or arylalkyl, are reacted with a 3-(1-hydroxyphenyl-1-methoximinomethyl)dioxazine of the general formula (V), if appropriate in the presence of a diluent and if appropriate in the presence of an acid acceptor.

The formula (VI) provides a general definition of the 4-halogeno-2-alkylsulphonylpyrimidines required as starting materials for carrying out the process c) according to the invention. In this formula (VI), X preferably or in particular has those meanings which have already been mentioned in connection with the description of the intermediates of the formula (II) according to the invention as being preferred or as being particularly preferred for X. $R^2$ represents alkyl or arylalkyl, preferably methyl or benzyl.

The 4-halogeno-2-alkylsulphonylpyrimidines of the formula (VI) are known and can be prepared by known processes (compare, for example, WO 95-24396).

The formula (V) provides a general definition of the 3-(1-hydroxyphenyl-1-alkoximinomethyl)dioxazines furthermore required as starting materials for carrying out the process c) according to the invention. In this formula (V), $E^1$, $E^2$, $E^3$, $E^4$, $L^1$, $L^2$, $L^3$ and $L^4$ preferably or in particular have those meanings which have already been mentioned in connection with the description of the compounds of the formula (I) according to the invention as being preferred or as being particularly preferred for $E^1$, $E^2$, $E^3$, $E^4$, $L^1$, $L^2$, $L^3$ and $L^4$.

The 3-(1-hydroxyphenyl- 1-alkoximinomethyl) dioxazines of the formula (V) are known and can be prepared by known processes (compare, for example, WO 95-04728).

Formula (III) provides a general definition of the nucleophilic compounds furthermore required as starting materials for carrying out the process a) according to the invention. In this formula (II), R and Q preferably or in particular have those meanings which have already been mentioned in connection with the description of the compounds of the formula (I) according to the invention as being preferred or as being particularly preferred for R and Q.

The nucleophilic compounds of the formula (III) are known chemicals for synthesis. The formula (IV) provides a general definition of the alkylsulphonylpyrimidines required as starting materials for carrying out the process b) according to the invention. In this formula (IV), R and Q preferably or in particular have those meanings which have already been mentioned in connection with the description of the compounds of the formula (I) according to the invention as being preferred or as being particularly preferred for R and Q. $R^1$ represents alkyl, or arylalkyl, preferably methyl or benzyl.

The alkylsulphonylpyrimidines of the formula (IV) are known and can be prepared by known processes (compare, for example WO 95-24396).

The 3-(1-hydroxyphenyl- 1-alkoximinomethyl) dioxazines furthermore required as starting materials for carrying out the process b) according to the invention have already been described further above in the description of the process c) according to the invention.

Suitable diluents for carrying out the processes a), b) and c) according to the invention are all inert organic solvents. These preferably include ethers, such as diethyl ether, diisopropyl ether, methyl-t-butyl ether, methyl-t-amyl ether, dioxane, tetrahydrofuran, 1,2- dimethoxyethane, 1,2-diethoxyethane or anisole; nitriles, such as acetonitrile, propionitrile, n- or i-butyronitrile or benzonitrile; amides, such as N,N,-dimethylformamide, N,N-dimethylacetamide, N-methylformanilide, N-methylpyrrolidone or hexamethylphosphoric triamide; sulfoxides, such as dimethylsulfoxide; or sulfones, such as sulfolane.

The processes a), b) and c) according to the invention are, if appropriate, carried out in the presence of a suitable acid acceptor. Suitable acid acceptors are customary inorganic or organic bases. These preferably include alkaline earth metal or alkali metal hydrides, amides, hydroxides, alcoholates, carbonates, bicarbonates, and also alkaline earth metal or alkali metal alkyl compounds, such as, for example, sodium hydride, sodium amide, potassium tert-butoxide, sodium hydroxide, potassium hydroxide, sodium carbonate, potassium carbonate, potassium bicarbonate, sodium bicarbonate or butyllithium.

When carrying out the processes a), b) and c) according to the invention, the reaction temperature can be varied within a relatively wide range. In general, the processes are carried out at temperatures from −20° C. to 130° C., preferably at temperatures from −10° C. to 80° C.

For carrying the process a) according to the invention for preparing the compounds of the formula (I), generally 0.5 to 5 mol, preferably 0.8 to 2 mol, of a nucleophilic compound of the formula (III) are employed per mole of 4-halogeno-2-phenoxypyrimidine of the formula (II).

For carrying out the process b) according to the invention for preparing the compounds of the formula (I), generally 0.5 to 5 mol, preferably 0.8 to 2 mol, of a 3-(1-hydroxyphenyl-1-methoximinomethyl)dioxazine of the formula (V) are employed per mole of alkylsulphonylpyrimidine of the formula (IV).

For carrying out the process c) according to the invention for preparing the compounds of the formula (II), generally 0.5 to 5 mol, preferably 0.8 to 2 mol, of a 3-(1-hydroxyphenyl-1-methoximinomethyl)dioxazine of the formula (V) are employed per mole of 4-halogeno-alkylsulphonylpyrimidine of the formula (VI).

The processes according to the invention are generally carried out under atmospheric pressure. However, it is also possible to operate under elevated or reduced pressure—generally between 0.1 bar and 10 bar.

The practice of the reaction and the work-up and isolation of the reaction products are carried out by generally customary processes (compare also the Preparation Examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, diseases in viticulture and fruit and vegetable growing, such as, for example, against Spaerotheca and Plasmopora species, or rice diseases, such as, for example, against Pyricularia species.

Furthermore, the compounds according to the invention may also be employed to increase the yield of crops. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood.

Microorganisms capable of degrading or changing the industrial materials which may be mentioned are, for example, bacteria, fungi, yeasts, algae and slime organisms. The active compounds or compositions according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components. Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichiamide, tricyclazole, tridemorph, triflumnizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H- 1,2,4-triazole- 1-ethanol,

α-(2,4-dichlorophenyl)-β-fluoro-b-propyl-1H-1,2,4-triazole- 1-ethanol,

α-(2,4-dichlorophenyl)-β-methoxy-a-methyl-1H-1,2,4-triazole- 1-ethanol,

α-(5-methyl- 1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}carbamate, 1-(2,4-dichlorophenyl)-2-(1H-1,2,4-triazol- 1-yl)ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)- 1,3-dioxolan-2-yl]-methyl]-1H-imidazole, 1-[[2-(4-chlorophenyl)-3-phenyloxiranyl]-methyl]-1H- 1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl ]-methyl]-benzamide, 2-(2,3,3-triiodo-2-propenyl)-2H-tetrazole, 2- [(1-methylethyl)sulphonyl]-5-(trichloromethyl)- 1,3,4-thiadiazole, 2- [[6-deoxy-4-O-(4-O-methyl-β-D-glycopyranosyl )-a-D-glucopyranosyl ]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl- 1-oxo- 1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo [1,5-a]quinazolin-5(4H)-one, 8-(1,1-dimethylethyl)-N-ethyl-N-propyl-1,4-dioxaspiro [4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2, 5-thiophenedicarboxylate, cis-1-(4-chlorophenyl)-2-(1H-1,2,4-triazol- 1-yl)-cycloheptanol, cis-4-[3-[4-(1,1-dimethylpropyl)-phenyl-2-methylpropyl]-2,6-dimethylmorpholinehydrochloride, ethyl [(4-chlorophenyl)-azo]-cyanoacetate, potassium hydrogen carbonate, methanetetrathiol sodium salt, methyl1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro4-nitrophenyl)4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazoldinyl)-acetamide,
N-(6-methoxy)-3-pyridinyl)-cyclopropanecarboxamide,
N- [2,2,2-trichloro-1-[(chloroacetyl)-amino]-ethyl]-benzamide,
N-[3-chloro4,5-bis(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
0-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl )-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the applications rates of active compounds are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rate of active compound are generally between 0.1 and 10,000 g/ha, preferably between 1 and 5000 g/ha.

The compositions used for the protection of industrial materials generally comprise an amount of 1 to 95%, preferably 10 to 75%, of the active compounds.

The use concentration of the active compounds according to the invention depend on the species and the occurrence of the microorganisms to be controlled and on the composition of the material to be protected. The optimum rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in the protection of materials, or of the compositions, concentrates or quite generally formulations preparable therefrom, can be increased by, if appropriate, adding other antimicrobially active compounds, fungicides, bactericides, herbicides, insecticides or other active compounds for broadening the activity spectrum or obtaining particular effects, such as, for example, the additional protection against insects. These mixtures may have a broader activity spectrum than the compounds according to the invention.

Preparation Examples

EXAMPLE (1)

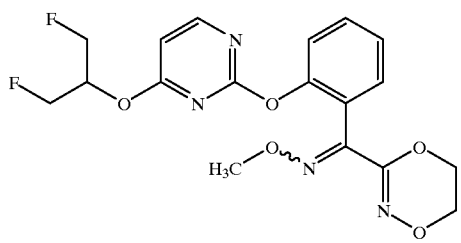

Process a)

A mixture of 1.5 g (0.0028 mol) of [2-(4-chloro-pyrimidin-2-yloxy)-phenyl]-(5,6-dihydro-[1,4,2]dioxazin-3-yl)-methanone O-methyl oxime, 0.3 g (0.0034 mol) of 1,3-difluoropropan-2-ol and 0.5 g of potassium carbonate in 20 ml of dry acetonitrile is stirred at 50° C. overnight. After cooling to room temperature, the mixture is concentrated under reduced pressure and the residue is taken up in ethyl acetate. The solution is washed twice with water, dried over sodium sulphate and concentrated under reduced pressure. The residue is chromatographed over silica gel using hexane/acetone (8:2). This gives 0.8 g of (70% of theory) of (5,6-dihydro-[1,4,2]dioxazin-3-yl)-{2-[4-(2-fluoro-1-fluoromethyl-ethoxy)-pyrimidin-2-yloxy]-phenyl}-methanone O-methyl oxime.

HPLC: logP=2.2

Preparation of the Starting Material

EXAMPLE (II-1)

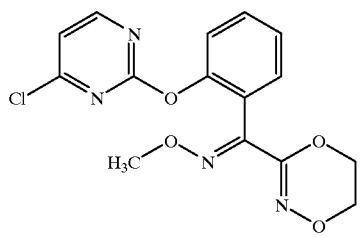

A mixture of 1.9 g (0.01 mol) of 4-chloro-2-methylsulphonylpyrimidine, 2.4 g (0.01 mol) of (5,6-dihydro-[1,4,2]dioxazin-3-yl)-(2-hydroxy-phenyl)-methanone O-methyl oxime and 1.7 g of potassium carbonate in 30 ml of dry acetonitrile is stirred at 50° C. overnight. After cooling to room temperature, the mixture is concentrated under reduced pressure and the residue is taken up in ethyl acetate. The solution is washed twice with water, dried over sodium sulphate and concentrated under reduced pressure. The residue is chromatographed over silica gel using hexane/acetone (8:2). This gives 1.5 g (43% of theory) of [2-(4-chloro-pyrimidin-2-yloxy)-phenyl]-(5,6-dihydro-[1,4,2]dioxazin-3-yl)-methanone O-methyl oxime.

HPLC: logP =2.0

EXAMPLE (2)

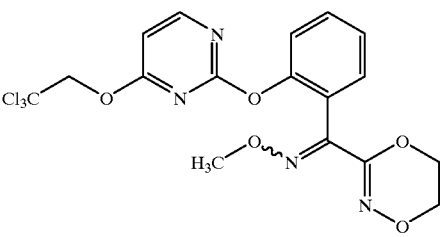

Process b)

At 0° C., 2.0 g (0.009 mol) of (5,6-dihydro-[1,4,2]dioxazin-3-yl)-(2-hydroxy-phenyl)-methanone O-methyl oxime are added to 0.3 g (0.009 mol) of sodium hydride (80% in mineral oil) in 30% of dry dimethylformamide. After evolution of hydrogen has ceased, 2.6 g (0.009 mol) of 4-(2,2,2-trichloroethoxy)-2-methylsulphonylpyrimidine are added a little at a time. The mixture is stirred overnight and subsequently concentrated under reduced pressure. The residue is taken up in ethyl acetate, and the solution is washed twice with water, dried over sodium sulphate and concentrated under reduced pressure. The residue is chromatographed over silica gel using hexane/acetone (7:3). This gives 1.45 g (34% of theory) of (5,6-dihydro-[1,4,2]dioxazin-3-yl)-{2-[4-(2,2,2-trichloroethoxy)-pyrimidine-2-yloxy]-phenyl}-methanone O-methyl oxime.

HPLC:logP=3.1

The compounds of the formula (1-a) according to the invention listed in Table 1 below are also obtained similarly to Examples (1) and (2), and in accordance with the general description of the preparation process a) and b) according to the invention:

(I-a)

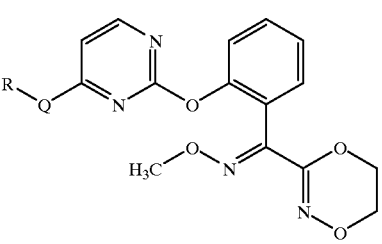

TABLE 1

| Example | Q | R | M.p. (° C.) | LogP |
|---|---|---|---|---|
| 3 | O | —CH$_2$—CF$_3$ | | 2.6 |
| 4 | O | 1,1,1-trifluoroprop-2-yl | | 2.9 |
| 5 | O | —C$_2$H$_5$ | 110–112 | 2.2 |
| 6 | O | -n-propyl | 88 | 2.5 |
| 7 | O | -i-propyl | | 2.5 |
| 8 | O | —CH$_2$—CF$_2$—CF$_3$ | | 3.1 |

TABLE 1-continued

| Example | Q | R | M.p. (° C.) | LogP |
|---|---|---|---|---|
| 9 | O | n-butyl | | 3.0 |
| 10 | O | —CH$_2$—CHCl$_2$ | 123 | 2.7 |
| 11 | O | —CH$_2$—CBr$_3$ | | 3.2 |
| 12 | O | benzyl | | 2.9 |
| 13 | O | n-hexyl | | 3.8 |
| 14 | O | n-pentyl | | 3.3 |
| 15 | O | 2-fluorobenzyl | | 2.9 |
| 16 | O | 4-methylbenzyl | | 3.2 |
| 17 | O | 2-(2-fluorophenyl)ethyl | | 3.2 |
| 18 | O | n-heptyl | | 4.2 |
| 19 | O | 3-fluorobenzyl | | 3.0 |
| 20 | O | 2(2-trifluoromethylphenyl)-ethyl | 151–53 | 3.6 |
| 21 | O | 1-phenylethyl | | 3.1 |
| 22 | O | 4-chlorobenzyl | | 3.3 |
| 23 | O | n-octyl | | 4.7 |
| 24 | O | 1-(2-chlorophenyl)-ethyl | | 3.4 |
| 25 | O | 2-phenylethyl | 137 | 3.3 |
| 26 | O | 2-(4-chlorophenyl)-ethyl | | 3.5 |
| 27 | O | cyclohexyl | | 3.3 |
| 28 | O | i-butyl | | |
| 29 | O | 2-butyl | | 2.90 |
| 30 | O | 3-methylbutyl | | |
| 31 | O | t-butyl | | |
| 32 | O | 4-methylpentyl | | |
| 33 | O | 3-methylpentyl | | |
| 34 | O | 2-methylpentyl | | |
| 35 | O | n-nonyl | | 5.10 |
| 36 | O | n-decyl | | 5.60 |
| 37 | O | n-dodecyl | | |
| 38 | O | —CH$_2$—CH$_2$F | | 2.00 |
| 39 | O | —CH$_2$—CHF$_2$ | | |
| 40 | O | —C$_2$F$_5$ | | |
| 41 | | —CH$_3$ | | |
| 42 | O | 1,1,1,3,3,3-hexafluoroprop-2-yl | | 3.30 |
| 43 | O | -n-C$_3$F$_7$ | | |
| 44 | O | —CHCl—CCl$_3$ | | |
| 45 | O | —C$_2$Cl$_5$ | | |
| 46 | O | —CH$_2$—CH$_2$—CCl$_3$ | | |
| 47 | O | —CH$_2$—CHBr$_2$ | | |
| 48 | O | allyl | | 2.40 |
| 49 | O | —CH$_2$—CCl=CCl$_2$ | | |
| 50 | O | but-2-en-1-yl | | |
| 51 | O | but-2-in-1-yl | | |
| 52 | O | —CH$_2$—CH$_2$—O—CH$_3$ | | |
| 53 | O | —CH$_2$—CH$_2$—O—C$_2$H$_5$ | | |
| 54 | O | cyclopentyl | | 3.00 |
| 55 | O | cyclobutyl | | |
| 56 | O | cycloheptyl | | |
| 57 | O | cyclohexylmethyl | | |
| 58 | O | cyclopentylmethyl | | 3.4 |
| 59 | O | cyclopropylmethyl | | 2.50 |
| 60 | O | 2-cyclohexylethyl | | |
| 61 | O | 4-fluorobenzyl | | |
| 62 | O | 4-ethylbenzyl | | |
| 63 | O | 4-phenylbenzyl | | |
| 64 | O | 4-phenoxybenzyl | | |
| 65 | O | 4-bromobenzyl | | |
| 66 | O | 3-methylbenzyl | | |
| 67 | O | 2-methylbenzyl | | |
| 68 | O | 3-chlorobenzyl | | |
| 69 | O | 2-chlorobenzyl | | |
| 70 | O | 4-ethoxybenzyl | | |
| 71 | O | 4-(n-propyl)benzyl | | |
| 72 | O | 4-trifluoromethylbenzyl | | |
| 73 | O | 3-trifluoromethylbenzyl | | |
| 74 | O | 2-trifluoromethylbenzyl | | |
| 75 | O | 2-methoxybenzyl | | |
| 76 | O | 4-nitrobenzyl | | |
| 77 | O | 4-cyanobenzyl | | |
| 78 | O | 1-(3-chlorophenyl)-ethyl | | |
| 79 | O | 1-(4-chlorophenyl)-ethyl | | |
| 80 | O | 1-(2-methylphenyl)-ethyl | | |
| 81 | O | 1-(3-methylphenyl)-ethyl | | |
| 82 | O | 1-(4-methylphenyl)-ethyl | | |
| 83 | O | 1-(4-methoxyphenyl)-ethyl | | |
| 84 | O | 1-(4-bromophenyl)-ethyl | | |
| 85 | O | 1-(3-trifluoromethylphenyl)-ethyl | | |

TABLE 1-continued

| Example | Q | R | M.p. (° C.) | LogP |
|---|---|---|---|---|
| 86 | O | 3-chloro-4-methylbenzyl | | 3.70 |
| 87 | O | 3-chloro-2-methylbenzyl | | |
| 88 | O | 2,4-dimethylbenzyl | | |
| 89 | O | 3,4-dimethylbenzyl | | |
| 90 | O | 2,4,6-trimethylbenzyl | | |
| 91 | O | 2-(4-methylphenyl)-ethyl | | |
| 92 | O | 2-(4-fluorophenyl)-ethyl | | |
| 93 | O | 2-(4-bromophenyl)-ethyl | | |
| 94 | O | 2-(4-trifluoromethylphenyl)-ethyl | | |
| 95 | O | 2-(3-trifluoromethylphenyl)-ethyl | | |
| 96 | O | 2-(3-methylphenyl)-ethyl | | |
| 97 | O | 2-(2-methylphenyl)-ethyl | | |
| 98 | O | 2-(4-methoxyphenyl)-ethyl | | 3.00 |
| 99 | O | 2-(3-chlorophenyl)-ethyl | | |
| 100 | O | 2-(2-chlorophenyl)-ethyl | | |
| 101 | O | 3-phenylpropyl | | 3.40 |
| 102 | O | 1-phenylprop-2-yl | | |
| 103 | O | 2-phenylpropyl | | |
| 104 | O | 4-phenylbutyl | | |
| 105 | O | 3-phenylbutyl | | |
| 106 | O | naphth-2-ylmethyl | | |
| 107 | O | naphth-1-ylmethyl | | |
| 108 | S | —CH$_3$ | | 2.2 |
| 109 | S | —C$_2$H$_5$ | | |
| 110 | S | n-propyl | | |
| 111 | S | i-propyl | | |
| 112 | S | n-butyl | | |
| 113 | S | 2-butyl | | |
| 114 | S | i-butyl | | |
| 115 | S | t-butyl | | |
| 116 | S | n-pentyl | | |
| 117 | S | n-hexyl | | |
| 118 | S | n-heptyl | | |
| 119 | S | n-octyl | | |
| 120 | S | benzyl | | 3.14 |
| 121 | S | 4-chlorobenzyl | | |
| 122 | S | 4-methylbenzyl | | |
| 123 | S | 2-phenylethyl | | |
| 124 | NH | —CH$_3$ | | |
| 125 | NH | —C$_2$H$_5$ | | |
| 126 | NH | n-propyl | | |
| 127 | NH | i-propyl | | |
| 128 | NH | n-butyl | | |
| 129 | NH | 2-butyl | | |
| 130 | NH | i-butyl | | |
| 131 | NH | t-butyl | | |
| 132 | NH | n-pentyl | | |
| 133 | NH | n-hexyl | | |
| 134 | NH | n-heptyl | | |
| 135 | NH | n-octyl | | |
| 136 | NH | benzyl | | 1.60 |
| 137 | NH | 4-chlorobenzyl | | |
| 138 | NH | 4-methylbenzyl | | |
| 139 | NH | 2-phenylethyl | | 2.40 |
| 140 | N(CH$_3$) | —CH$_3$ | | |
| 141 | N(CH$_3$) | —C$_2$H$_5$ | | |
| 142 | N(CH$_3$) | n-propyl | | |
| 143 | N(CH$_3$) | i-propyl | | |
| 144 | N(CH$_3$) | n-butyl | | |
| 145 | N(CH$_3$) | 2-butyl | | |
| 146 | N(CH$_3$) | i-butyl | | |
| 147 | N(CH$_3$) | t-butyl | | |
| 148 | N(CH$_3$) | n-pentyl | | |
| 149 | N(CH$_3$) | n-hexyl | | |
| 150 | N(CH$_3$) | n-heptyl | | |
| 151 | N(CH$_3$) | n-octyl | | |
| 152 | N(CH$_3$) | benzyl | | 1.84 |
| 153 | N(CH$_3$) | 4-chlorobenzyl | | |
| 154 | N(CH$_3$) | 4-methylbenzyl | | |
| 155 | N(CH$_3$) | 2-phenylethyl | | |
| 156 | O | 4-methoxybenzyl | | 2.80 |
| 157 | O | 2,2,3,3-tetrafluoropropyl | | 2.60 |
| 158 | O | 3,3,3-trifluoropropyl | | 2.60 |
| 159 | O | 5-phenylpentyl | | 4.10 |
| 160 | O | propargyl | | 2.10 |
| 161 | O | 3-phenylallyl | | 3.30 |

TABLE 1-continued

| Example | Q | R | M.p. (° C.) | LogP |
|---|---|---|---|---|
| 162 | O | (2-methylprop-1-enyl)-2,2-dimethyl-3-ethylcyclopropyl | | 4.30 |
| 163 | O | —$C_{16}H_{33}$ | | >7.4 |
| 164 | O | 2-methylbut-3-en-2-yl (isopropenyl-methyl) | | 2.70 |
| 165 | O | hexa-2,4-dienyl | | 3.20 |
| 166 | O | pent-2-enyl | | 2.70 |
| 167 | O | 2-chloro-3,3,4-trifluorocyclobutylmethyl | | 3.00 |
| 168 | O | 4-methylthiobenzyl | | 2.10 |
| 169 | O | 2-bromobut-1-en-... | | 2.70 |
| 170 | O | hex-3-enyl | | 3.20 |
| 171 | NH | 1-phenylethyl | | 1.80 |
| 172 | O | 1,2-dichloro-1-methyl-2-ethylcyclopropyl | | 3.30 |

Use Examples

EXAMPLE A

Erysiphe test (barley)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. hordei.

The plants are placed in a greenhouse at a temperature of approximately 20° C. and a relative atmospheric humidity of approximately 80% to promote the development of mildew postules.

Evaluation is carried out 7 days after the inoculation. 0% means an efficacy which corresponds to that of the control, whereas an efficacy of 100% means that no infection is observed.

In this test, for example, the compound of Preparation Example (3) exhibits, at an exemplary active compound application rate of 250 g/ha, an efficacy of 100% in comparison to the untreated control.

TABLE A

Erysiphe test (barley)/protective

| Active compound | Application rate of active compound in g/ha | Efficacy in % |
|---|---|---|
| (3) | 250 | 100 |

EXAMPLE B

Erysiphe test (barley)/curative

Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amount of solvent and emulsifier, and the concentrate is diluted with water to the desired concentration.

To test for curative activity, young plants are dusted with spores of Erysiphe graminis f.sp. hordei. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew postures.

Evaluation is carried out 7 days after the inoculation. 0% means an efficacy which corresponds to that of the control, where an efficacy of 100% means that no infection is observed.

In this test, for example, the compounds of Preparation Examples (3) and (6) exhibit, at an exemplary active compound application rate of 250 g/ha, an efficacy of 100% in comparison to the untreated control.

TABLE B

Erysiphe test (barley)/curative

| Active compound | Application rate of active compound in g/ha | Efficacy in % |
|---|---|---|
| (3) | 250 | 100 |
| (6) | 250 | 100 |

EXAMPLE C

Erysiphe test (barley)/protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. hordei.

The plants are placed in a greenhouse at a temperature of approximately 20° C. and a relative atmospheric humidity of approximately 80% to promote the development of mildew postules.

Evaluation is carried out 7 days after the inoculation. 0% means an efficacy which corresponds to that of the control, whereas an efficacy of 100% means that no infection is observed.

In this test, for example, the compound of Preparation Example (13) exhibits, at an exemplary active compound application rate of 250 g/ha, an efficacy of 100% in comparison to the untreated control.

EXAMPLE D

Plasmopara test (grapevine)/protective

Solvent: 47 parts by weight of acetone

Emulsifier: 3 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at approximately 20° C. and 100 % relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to the control, whereas an efficacy for 100% means that no infection is observed.

In this test, for example, the compounds of Preparation Examples (1), (2), (3), (7), (8), (9), (10), (11), (12), (13) and (14) exhibit, at an exemplary active compound application rate of 100 g/ha, an efficacy of up to 100% in comparison to the untreated control.

TABLE C

Erysiphe test (barley)/protective

| Active compound | Application rate of active compound in g/ha | Efficacy in % |
| --- | --- | --- |
| 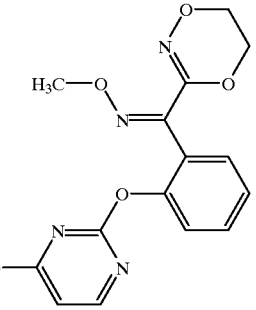 (13) | 250 | 100 |

TABLE D

Plasmopara test (grapevine)/protective

| Active compound | Application rate of active compound in g/ha | Efficacy in % |
|---|---|---|
| (3) | 100 | 97 |
| (7) | 100 | 100 |
| (2) | 100 | 94 |
| (8) | 100 | 100 |
| (9) | 100 | 100 |

TABLE D-continued
Plasmopara test (grapevine)/protective
| Active compound | Application rate of active compound in g/ha | Efficacy in % |
|---|---|---|
| 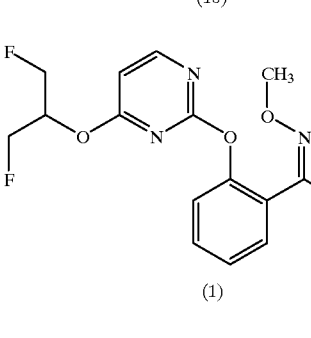 (10) | 100 | 92 |
| 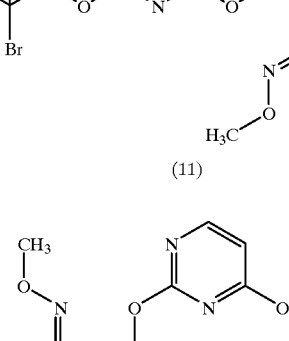 (1) | 100 | 89 |
| 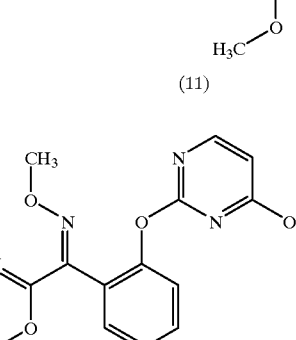 (11) | 100 | 100 |
| 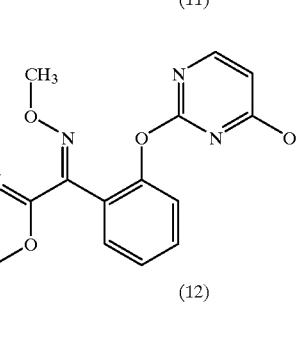 (12) | 100 | 100 |
| 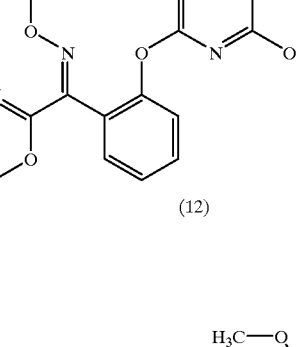 (13) | 100 | 100 |

TABLE D-continued

Plasmopara test (grapevine)/protective

| Active compound | Application rate of active compound in g/ha | Efficacy in % |
|---|---|---|
| 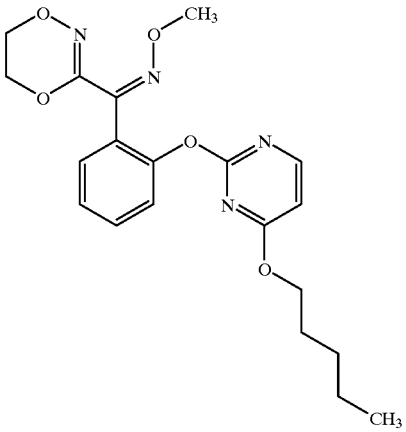<br>(14) | 100 | 99 |

EXAMPLE E

Sphaerotheca test (cucumber)/protective

Solvent: 47 parts by weight of acetone

Emulsifier: 3 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating is dried on, the plants are inoculated with an aqueous spore suspension of Sphaerotheca fuliginea. The plants are then placed in a greenhouse at approximately 23° C. and a relative atmospheric humidity of approximately 70%.

Evaluation is carried out 10 days after the inoculation. 0% means an efficacy which corresponds to further control, whereas an efficacy of 100% means that no infection is observed.

In this test, for example, the compounds of Preparations Examples (2), (6) and (8) exhibit, at an exemplary active compound application rate of 100 g/ha, an efficacy of more than 90% in comparison to the untreated control.

TABLE E

Sphaerotheca test (cucumber)/protective

| Active compound | Application rate of active compound in g/ha | Efficacy in % |
|---|---|---|
| 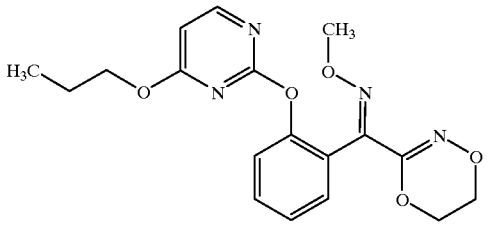<br>(6) | 100 | 94 |

TABLE E-continued

Sphaerotheca test (cucumber)/protective

| Active compound | Application rate of active compound in g/ha | Efficacy in % |
|---|---|---|
| 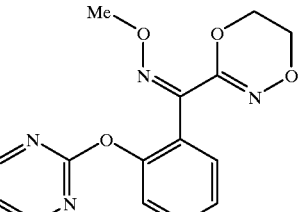 (2) | 100 | 96 |
| 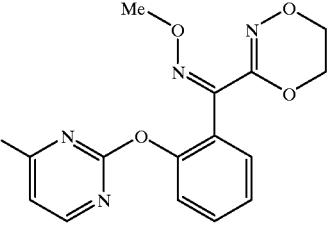 (8) | 100 | 92 |

EXAMPLE F

Pyricularia test (rice)/protective

Solvent: 2.5 parts by weight of acetone

Emulsifier: 0.06 part by weight of alkylaryl polyglycol ether

To produce a suitable preparation of active compound, 1 part by weight of active compound is mixed with the stated amount of solvent and the concentrate is diluted with water and the stated amount of emulsifier to the desired concentration.

To test for protective activity, young rice plants are sprayed with the preparation of active compound at the stated application rate. After the spray coating has dried on, the plants are inoculated with an aqueous spore suspension of Pyricularia oryzae. The plants are subsequently placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, for example, the compounds of Preparation Examples (3), (5) and (6) exhibit, at an exemplary active compound application rate of 750 g/ha, an efficacy of at least 70% in comparison to the untreated control.

TABLE F

Pyricularia test (rice)/protective

| Active compound | Application rate of active compound in g/ha | Efficacy in % |
|---|---|---|
| 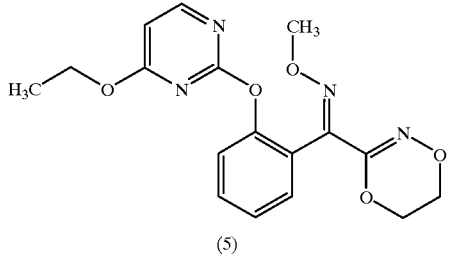 (5) | 750 | 80 |

TABLE F-continued

Pyricularia test (rice)/protective

| Active compound | Application rate of active compound in g/ha | Efficacy in % |
|---|---|---|
| (6) | 750 | 90 |
| (3) | 750 | 70 |

What is claimed is:

1. A compound of the formula (I)

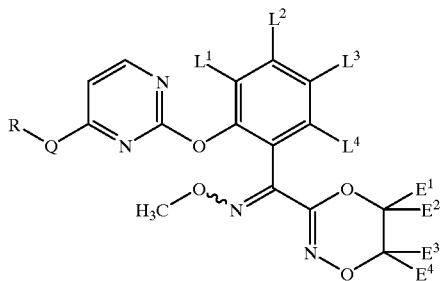

(I)

in which

R
  represents methyl which is substituted with from zero to three halogen atoms and is substituted with zero or one cycloalkyl having 3 to 6 carbon atoms, where the cycloalkyl group is unsubstituted or is substituted by 1 to 4 halogen atoms and/or 1 to 3 alkyl groups having 1 to 3 carbon atoms, or
  represents alkyl, alkenyl or alkinyl, each of which has 2 to 12 carbon atoms, and each of which is substituted with a member selected from the group consisting of from zero to n halogen atoms (where n represents the number of the hydrogen atoms of the unsubstituted hydrocarbon radical in question) from zero to 2 alkoxy groups having 1 to 8 carbon atoms and from zero to 2 cycloalkyl groups having 3 to 6 carbon atoms, wherein said cycloalkyl groups are unsubstituted or are substituted with from 1 to 4 halogen atoms and with from zero to 3 alkyl groups having 1 to 3 carbon atoms, or
  represents cycloalkyl having 3 to 8 carbon atoms which is substituted with from zero to five moieties selected from the group consisting of alkyl having 1 to 4 carbon atoms, halogen and alkoxy having 1 to 4 carbon atoms or
  represents arylalkyl or arylalkenyl having 1 to 5 carbon atoms in the alkyl moiety and 2 to 5 carbon atoms in the alkenyl moiety, respectively, and 6 to 10 carbon atoms in the aryl moiety, which aryl moiety is substituted with from zero to five substituents selected from the group consisting of
    halogen, cyano, nitro, amino, hydroxyl, formyl, carboxyl, carb-amoyl, thiocarbamoyl;
    alkyl, alkoxy, alkylthio, alkylsulphinyl or alkylsulphonyl having in each case 1 to 6 carbon atoms;
    alkenyl or alkenyloxy having in each case 2 to 6 carbon atoms;
    halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
    halogenoalkenyl or halogenoalkenyloxy having in each case 2 to 6 carbon atoms and 1 to 11 identical or different halogen atoms;
    alkylamino, dialkylamino, alkylcarbonyl, alkylcarbonyloxy, alkoxycarbonyl or alkylsulphonyloxy, having in each case 1 to 6 carbon atoms in the individual alkyl moieties;
    in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 t o 9 identical or different halogen atoms;

cycloalkyl having 3 to 8 carbon atoms;

heterocyclyl or heterocyclyl-methyl having in each case 3 to 7 ring members, 1 to 3 of which are in each case identical or different heteroatoms, selected from the group consisting of nitrogen, oxygen and sulphur and a grouping

in which
A$^1$ represents alkyl having 1 to 4 carbon atoms or cycloalkyl having 1 to 6 carbon atoms and
A$^2$ represents unsubstituted or cyano-, alkoxy-, alkylthio-, alkylamino-, dialkylamino- or phenyl-substituted alkyl having 1 to 4 carbon atoms, alkenyl or alkinyl having in each case 2 to 4 carbon atoms, Q represents oxygen, sulphur, —NH— or

where R$^1$ represents alkyl having 1to 4 carbon atoms,

E$^1$, E$^2$, E$^3$ and E$^4$ are identical or different and independently of one another represent hydrogen, alkyl having 1 to 4 carbon atoms or E$^1$ and E$^2$ or E$^1$ and E$^3$ or E$^3$ and E$^4$ together with the respective carbon atoms to which they are attached form a cycloaliphatic ring having 5, 6 or 7 carbon atoms and L$^1$, L$^2$, L$^3$ and L$^4$ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case substituted by from zero to 5 halogen atoms.

2. The compound of claim 1 in which

R
represents methyl which is substituted with from zero to three fluorine, chlorine or bromine atoms and with from zero to one cyclopropyl, cyclo-butyl, cyclopentyl or cyclohexyl groups, where the cycloalkyl groups are substituted with from zero to 4 fluorine, chlorine or bromine atoms and with from zero to 3 methyl or ethyl groups, or represents ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl, n-heptyl-, n-octyl-, n-nonyl-, n-decyl, n-undecyl, n-dodecyl, allyl, but-2-en-1-yl, but-1-en-3-yl, hex-2-en-1-yl, hexa-2,4-dien-1-yl, propargyl, but-2-in-1-yl, each of which is substituted with from zero to 3 groups selected from the group consisting of fluorine, chlorine or bromine and from zero to two groups selected from the group consisting of methoxy, ethoxy, cyclopropyl, cyclobutyl, cyclopentyl or cyclohexyl, wherein the cycloalkyl groups are substituted with from zero to 4 fluorine, chlorine or bromine atoms and with from zero to 3 methyl or ethyl groups), or represents cyclobutyl, cyclopentyl, cyclohexyl, cycloheptyl or cyclopropyl, each of which is substituted with from zero to 5 substituents selected from the group consisting of methyl, ethyl, n- or i-propyl, n-, i-, s- or t-butyl, fluorine, chlorine, bromine, methoxy and ethoxy or represents 1-phenylethyl, 2-phenylethyl, 1-phenylpropyl, 2-phenylpropyl, 3-phenylpropyl, 1-phenylprop-2-yl, 2-phenylprop-2-yl, 3-phenylbutyl, 4-phenylbutyl, 5-phenylpentyl, 3-phenylallyl, naphth-1-ylmethyl or naphth-2-ylmethyl or benzyl, each of which is substituted with from zero to five substituents in the phenyl or naphthyl moiety, where the substituents of the aryl moiety are selected from the group consisting of fluorine, chlorine, bromine, cyano, methyl, ethyl, n- or i-propyl, n-, i-, s- or t-butyl methoxy, ethoxy, n- or i-propoxy, methylthio, ethylthio, n- or i-propylthio, methylsulphinyl, ethylsuphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is substituted by identical or different substituents selected from the group consisting of fluorine, chlorine, methyl, trifluoromethyl and ethyl or a grouping

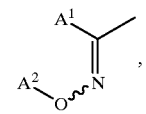

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methyl-aminoethyl or benzyl, Q represents oxygen, sulphur, —NH—,

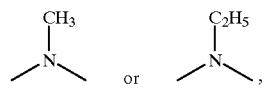

E$^1$, E$^2$, E$^3$ and E$^4$ are identical or different and independently of one another represent hydrogen, methyl, ethyl, n- or i-propyl, n-, i-, s- or t-butyl, or E$^1$ and E$^2$ or E$^1$ and E$^3$ or E$^3$ and E$^4$ together with the respective carbon atoms to which they are attached form a cycloaliphatic ring having 5, 6 or 7 carbon atoms and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methyl-sulphonyl or ethylsulphonyl, trifluoromethyl, trifluoroethyl, difluoro-methoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. The compound of claim 1 in which $E_1$, $E^2$, $E^3$, $E^4$, $L^1$, $L^2$, $L^3$ and $L^4$ represent hydrogen.

4. A pesticide composition comprising at least one pesticidally effective compound of the formula (I) according to claim 1 and one or more extenders and/or surfactants.

5. A method for controlling pests comprising applying compounds of the formula (I) according to claim 1 to pests and/or their habitat.

6. A process for preparing compounds of the formula (I) as defined in claim 1 comprising reacting 4-halogeno-2-phenoxypyrimidines of the formula (II)

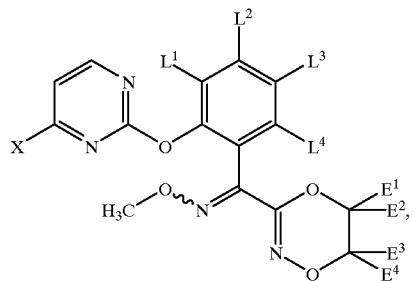
(II)

wherein $E^1$, $E^2$, $E^3$, $E^4$, $L^1$, $L^2$, $L^3$ and $L^4$ are as defined in claim 1 and X represents halogen, with a nucleophilic compound of the formula

R—Q—H (III), wherein

R and Q are as defined in claim 1, or reacting alkyl-sulphonylpyrimidines of the formula (IV)

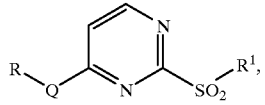
(IV)

wherein

R and Q are as defined in claim 1 and $R^1$ represents alkyl or arylalkyl, are reacted with a 3-(1-hydroxyphenyl-1-methoximinomethyl)dioxazine of the formula

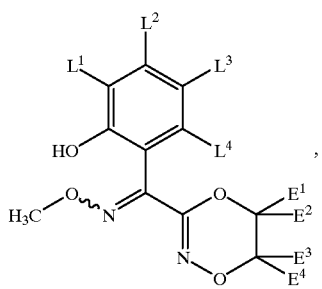
(V)

in which $E^1$, $E^2$, $E^3$, $E^4$, $L^1$, $L^2$, $L^3$ and $L^4$ are as defined in claim 1.

7. The compound of the formula (II)

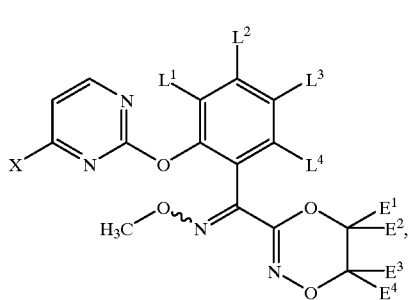
(II)

in which $L^1$, $L^2$, $L^3$, $L^4$, $E^1$, $E^2$, $E^3$ and $E^4$ are as defined in claim 1 and X represents halogen.

* * * * *